(12) United States Patent
Norton

(10) Patent No.: US 6,739,200 B1
(45) Date of Patent: May 25, 2004

(54) METHOD OF STRESS TESTING FOOTWEAR

(76) Inventor: Craig Norton, 6830 Ridgewood Rd., Oakland, CA (US) 94611

(*) Notice: Subject to any disclaimer, the term of this patent is extended or adjusted under 35 U.S.C. 154(b) by 0 days.

(21) Appl. No.: 10/245,658

(22) Filed: Sep. 18, 2002

(51) Int. Cl.[7] .............................. G01N 3/00; G01N 3/22
(52) U.S. Cl. .............................. 73/788; 73/794; 73/847
(58) Field of Search ......................... 73/597, 761, 786, 73/788, 847, 794

(56) References Cited

U.S. PATENT DOCUMENTS 6,289,743 B1   9/2001   Norton

*Primary Examiner*—Edward Lefkowitz
*Assistant Examiner*—Lilybett Martir

(74) *Attorney, Agent, or Firm*—Tom Hamill, Jr.

(57) ABSTRACT

A method of testing athletic shoes is provided. The testing subjects athletic shoes to different temperature conditions in one test or different kinetic forces in another test. After undergoing the stressor (temperature, kinetic forces, other) the axial resistance exhibited by the shoe is measured by placing the shoe in the shoe testing device. The device ascertains the amount of torque required to rotate or twist each shoe to a standard amount. These results permits the different models and brands of athletic shoe to be independently categorized and grouped based on their performance with relation to the different stressor placed on the shoe. This would then permit the consumer, health professional and/or consultant to choose an athletic shoe which would assist in correcting pain caused by various degrees of motion in the foot or lower leg. By utilizing the categorizations, along with the needs of the individual, one may select an athletic shoe which can treat the effects of pronation and improper gait.

17 Claims, 2 Drawing Sheets

METHOD OF STRESS TESTING FOOTWEAR

REFERENCE TO RELATED APPLICATION

Reference is made to issued U.S. Pat. No. 6,289,743 by the same inventor which is hereby incorporated by reference. This utility patent draws priority from provisional application 60/410,341, filed Sep. 13, 2002.

BACKGROUND OF THE INVENTION

1. Field of the Invention

The present invention relates generally to testing shoes, such as athletic shoes. The present invention relates to testing athletic shoes by first establishing a baseline of the shoe's resistance to rotational forces at a first temperature, and then by establishing a functional norm of the shoe's resistance to rotational forces at a second temperature at which it would be worn. These results would be quantified and grouped by the amount of resistance offered at the different conditions. Additional tests would subject the shoe to stress: i.e. a higher than normal temperature, or to wear the shoe for a set time or distance and then to again compare the resistance to axial torque in relation to both the baseline and functional norm. Based on these results, it would permit a consumer or advocate to determine what shoe is proper for the athlete or customer who will wear it.

2. Description of the Prior Art

As noted above, applicant's previous U.S. Pat. No. 6,289,743 is incorporated by reference and is directed towards a shoe testing apparatus. This apparatus allows for the person using it to determine the amount of resistance to an axial twisting motion subjected to an athletic shoe. This resistance is measured in inch-pounds. Any units of measurement for torque may be used, in both english and metric units.

This is important in that incorrect shoe selection and fitting can result in injury to the wearer. Particularly, a user whose foot exhibits a large amount of pronation is susceptible to such conditions as shin splints, plantar fascitis, posterior tibialis tendonitis and general knee pain. A pronated foot is characterized by a navicular drop of over 11 mm. The navicular bone is located in the medial midfoot and is the bone located distal to the talus and proximal the medial cuneform. Excessive pronantion may be caused by a habitual gait that rotates the tibia and femur in an inappropriate manner and may also be exacerbated by the weight of the runner or walker. The gait of the person in question is examined to estimate the amount the amount of pronation caused by the stance in the contact, midstance, and propulsion phases of walking, running, hiking, etc. Applicant's previous patent allows for various shoes to be tested in regards to axial rotation. The present invention improves on this technique by allowing various models of shoes to be tested after they have been subject to various real life stresses.

Athletic shoes of the type commonly purchased today have varying amounts of support. This support is affected by the material of the uppers, the boarded lasts of the shoe, and the materials used in the midsole, such as polyurethane, plastic, and EVA (Ethyl Vinyl Acetate). The present invention allows the user of applicant's apparatus (the '743 patent) to determine the amount of axial rotation that various brands of shoes allow after being subject to stress. Shoes "out of the bog" a resistance value (measured in inch-pounds) that may be markedly different at a higher temperature or after repetitive motion The present invention measures (first) a baseline value at, for example, 66 degrees Fahrenheit, then a functional value after being maintained at, for example 88 degrees Farenheit for a time period of, for example, 72 hours or so. Second, the present invention allows for the user to test the loss of resistance after a set period of activity, for example a 10 km run. In both cases, a fatigue factor, represented as a percentage loss of resistance to axial rotation may be determined from a number of shoes of Various models and brands.

SUMMARY OF THE INVENTION

The present invention provides a method of testing and comparing various types of athletic shoes under stress. Resistance to axial rotation is measured in inch-pounds at a baseline temperature. Then the shoe is subject to either environmental (temperature) stress or kinetic (repetitive motion) stress. After a set period of time at a certain temperature or after a set amount of physical activity while the shoes are being worn, the shoe is then again subjected to axial rotation and the resistance in inch-pounds is again measured. The percentage difference is registered as a fatigue factor and allows the user to determine the brand of shoe that would or would not be advantageous to a certain customer's or athlete's gait.

Other comparison tests may be performed. The shoes may be stressed by immersion in water, mud, bicycling, running, cross-country running and the like.

It is an object of the invention to provide a method of stress testing footwear wherein a baseline of resistance to axial rotation in an athletic shoe may be determined.

It is another object of the invention to provide a method of stress testing footwear wherein the user may determine an optimal shoe type or brand for a customer or athlete depending on an analysis of the various subphases of the stance during movement.

Yet another object of the invention is to provide a method of stress testing footwear wherein the user may determine the fatigue factor in the shoe represented by a percentage loss of resistance in inch-pounds after the shoe has undergone a predetermined amount of stress.

Yet another object of the invention is to provide a method of stress testing footwear wherein the fatigue factor is determined after the shoe has been maintained at a specific temperature for a specific period of time.

Still yet another object of the invention is to provide a method of stress testing footwear wherein the fatigue factor is determined after the shoe has been worn during a predetermined amount of exercise: i.e. running or walking a set distance, or participating in an athletic event for a certain period of time.

Yet another object of the invention is to provide a method of stress testing footwear wherein a large collection of data points may be determined for a specific brand of shoe so that the temperature of kinetic breakdown of the shoe support may be determined over time.

Still yet another object of the invention is to provide a method of stress testing footwear wherein a large collection of data points may be determined for various brands and models of shoes under the same type of predetermined stress and thus the user may determine which brand is optimal for a specific gait in an event or an environment.

These together with still other objects of the invention, along with the various features of novelty which characterize the invention, are pointed out with particularity in the claims annexed to and forming a part of this,disclosure. For a better understanding of the invention, its operating advantages and the specific objects attained by its uses, reference should be made to the accompanying drawings and descriptive matter in which there are illustrated preferred embodiments of the invention.

BRIEF DESCRIPTION OF THE DRAWINGS

The invention will be better understood and the above objects as well as objects other than those set forth above will become more apparent after a study of the following detailed description thereof. Such description makes reference to the annexed drawings wherein.

DESCRIPTION OF THE PREFERRED EMBODIMENTS

The present invention is a method of testing athletic footwear after it has been subject to stress and calculating a fatigue factor as a percentage of lost stability from a predetermined baseline. This technique allows the user to determine what the best brand or the type of shoe would be for an athlete or a customer depending on the observed qualities of their gait regarding foot pronation and the amount of environmental or kinetic stress that the footwear would be subjected to during usual activity.

Figure 1:
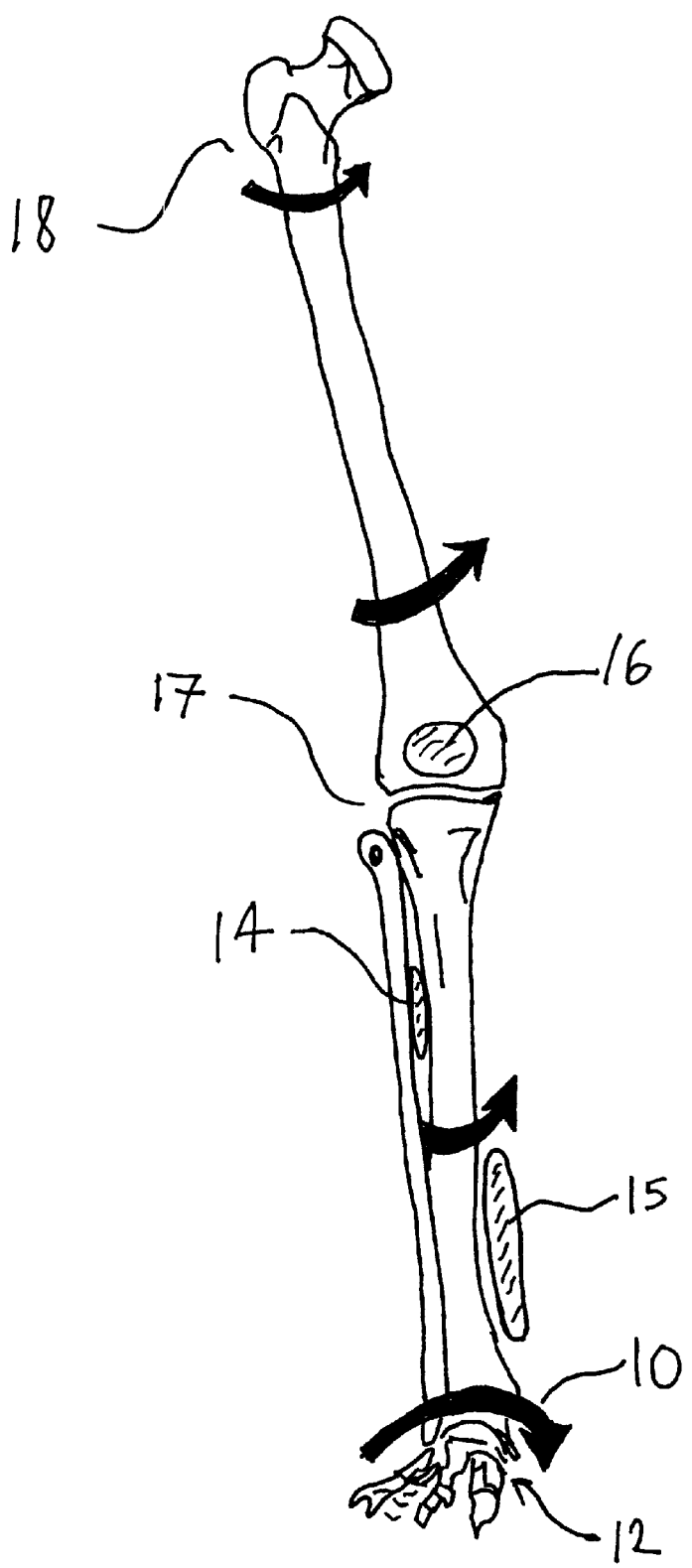
FIG. 1 is a view showing the various forces and how they act on the leg during harmful pronation of the foot during the subphases of a person's stance.

The stability of the shoe is basically how well a shoe supports the user's arch and heel and, especially in regards to the instant invention, counteracts the rotational forces of pronation. A pronated foot, or hyper-pronated foot can be characterized by a navicular drop of over 11 mm. This drop of the navicular, located between the talus (heel) and the metatarsals (toes) of the human foot can lead to a variety of conditions such as shin splints, plantar fasciitis, posterior tibialis tendonitis, and knee pain which will be discussed further hereinbelow under a section that refers to clinical observations made by applicant. Turn to FIG. 1 for a diagram demonstrating harmful pronation of the foot during the subphases of a person's stance. At 10 there is indicated the tibia rotation from the heel strike to full weight bearing. This is where posterior tibial tendonitis over the pronation may develop. The tibia rotates internally as the arch drops. At 12 is indicated the location of the navicular drop. Areas where what are called "shin splints" could develop are indicated at 14 and 15. 14 indicates the area of antero-lateral shin splints and 15 indicates the area where medial shin splints can develop. Areas that subsequent knee pain could develop in are indicated at 16 as the femur rotates internally over the arch drop. This can additionally cause llio-tibial band pain indicated in the area at 17. Generalised hip pain can also develop over pronation as indicated at 18. All of these problems are in some way addressable by preventing the pronation of the foot and the navicular drop that causes the stress. In some cases, the gait may be habitual or brought on by physical causes. In many cases, the weight of the athlete (runner, walker) exacerbates the problem. Proper support of the foot goes a long way towards addressing this problem. The instant invention is a method of ascertaining what kind or which brand of shoe is best for a certain person performing a specified activity.

Figure 2:
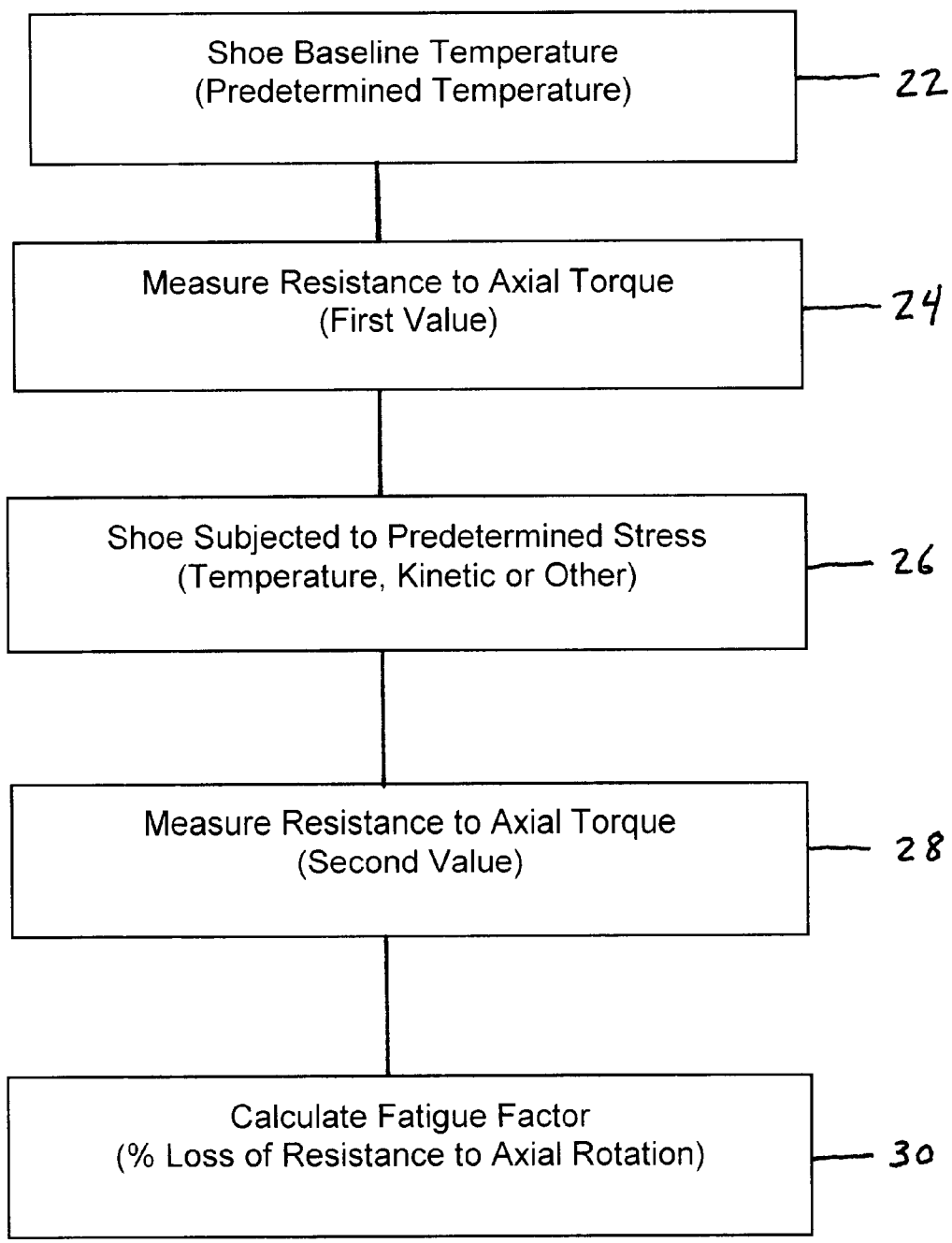
FIG. 2 is a block diagram of the method of the invention.

Turning to FIG. 2, the overall steps of the instant invention are generally designated at 20. The first step 22 is to establish a baseline. In the preferred embodiment described herein, this baseline is established at 66° F. It should be emphasized at this point that a wide range of temperatures could be used to set this baseline. Lower temperatures could be chosen if the athletic shoe was to be used in a sub arctic or arctic environment. Again, a skilled practitioner would find a wide range of baseline establishment temperatures to be workable. In the embodiment described herein, this baseline of 66° is set by first maintaining the shoe in a controlled environment for at least 72 hours. This amount of time gives every portion of the shoe, even the interior midsole a chance to reach the desired temperature. If desired, a thermometer (not shown) could be used to ascertain the temperature of the interior parts of the shoe. The shoe in question is then placed on the apparatus described in applicant's issued U.S. Pat. No. 6,289,743. This apparatus (incorporated by reference) allows the user to measure the resistance to axial torque in a desired direction. The reading is made in inch-pounds, but it should be noted that other scales could easily be used. On or more shoes can be tested in a sequence, with a plurality of brands to allow a multitude of data points to be collected at the desired baseline. This first measuring and recording step is indicated at 24 in FIG. 2.

The discussion now turns to the stress subjecting step which is indicated at 26 in FIG. 2. A wide variety of stresses can be put on the shoe. Two of them will be discussed in the embodiment described herein. The first is an environmental test, specifically a temperature test There are a number of reasons why this test is desirable. First, depending on the environment in which the shoe is going to be used, different ambient shoe temperatures can be expected. A sharp difference would be seen if the shoe were to be used for example during the month of July in Portland, Oreg. versus the same time period in Las Vegas, Nev. The second location would subject the shoe to a much higher ambient temperature. Thus, in the first environmental stressor step, the shoe is raised to a predetermined temperature and maintained at that temperature for a predetermined time. In one example of the invention, the shoe in question is placed in an environment of about 88° Fahrenheit and maintained in that environment for about 72 hours. It should be understood that these temperatures and times are only an example of one possible proposed test condition and should not be considered to be limiting the scope of the invention in any way. A skilled practitioner could use a spectrum of temperatures and times depending on the perceived environment in which the shoe was going to be used to get useful results from the apparatus. By comparing the torque produced at the first temperature versus the torque produced at the second temperature one can objectively measure and compare the different models and brands of athletic shoes. This gives an objective quality measurement for each model and brand of shoe which can then be employed to assist people with different shoe requirements. By selecting the correct shoe, one may reduce pain caused by pronation or improper gait. It is also to be understood that one of the main reasons that measurements are taken at a higher temperature is due to body heat and how it effects the shoe. The temperature at which the shoe is exposed to is related to body heat as well as external temperature.

The second stressor test would be a kinetic stressor. This basically would involve repetitive movement of the shoe to either simulate an athletic activity or to perform the athletic activity. The user could, for example, run a ten-kilometer course or play a half hour of soccer. Other activities could, of course, be used, or a mechanical mechanism (not shown) could manipulate the shoe.

Referring to reference numeral 28 of FIG. 2, the second measuring and recording step is shown. This is accomplished in the same manner as the first measuring and recording step 24. Again the scale is read out in inch-pounds but other values could be used.

Lastly, the calculation of the fatigue factor is accomplished. This factor is a percentage of the loss of resistance to axial rotation. This step is indicated at 30.

The discussion now turns to stability of various types of shoes and the classifications that applicant has developed for grouping them.

Level 1 Stability is for excessive pronators to moderate pronators. Moderate pronators who experience hip, knee, shin, foot, or ankle pain benefit from this level of stability. Runners who are moderate pronators and are of large or heavy stature or walkers who are moderate to excessive pronators and who experience hip, knee, shin, foot, or ankle pain also benefit from this, the highest level of stability with the most resistance to axial torque.

Level 2 Stability is for mild to moderate pronators who have no physical pain or for heavy runners with either neutral feet or mild pronation. Additionally, this level of stability is called for in supinators of heavy stature.

Level 3 Stability is for neutral to mild pronators who have no physical symptoms or for runners with neutral feet or mild pronation of light to moderate stature. Additionally, this level of stability is appropriate to supinators of light to moderate stature.

CLINICAL OBSERVATIONS

The discussion now turns to observed conditions and the shoe requirements and recommendations therefore. A plurality of tables of mens and womens shoes with exemplary test results were provided in the provisional application from which this utility application is based.

In the case of an athlete or customer of heavy stature, the shoe requirement would be maximum stability for support. Thus, a level 1 stability shoe would be recommended.

For moderate to excessive pronation, flat or "mobile" feet the requirement would be that the long axis of the shoe should provide maximum resistance to pronation. The shoe should also have a firm heel counter. This helps the foot become more rigid and increases its efficiency as a lever arm. A level 1 type shoe is recommended.

In the case of a supinated foot (the opposite of pronation), a rigid foot, or a foot that lacks natural cushioning, what is required is a firm heel counter with a soft midsole to provide the needed cushioning. A level 2 stability shoe is appropriate.

For someone with ankle instability, the shoe should have maximum resistance to pronation along the long axis of the shoe. The shoe should have a firm heel counter. These two features translate stability to the ankle. This calls for a level 1 stability shoe.

Knee pain or "runner's knee" which is associated with pronation also calls for the long axis of the shoe to have maximum resistance to pronation during the weight-bearing phase of the gait. This provides both better alignment for the patella and allows the quadriceps to work more efficiently. A level 1 stability shoe in recommended.

The ilio-tibial band syndrome is also associated with pronation. Again, the long axis of the shoe should have maximum resistance to foot rotation during the weigh-bearing phase of the gait. The slackens the ilio-tibial band which reduces friction and irritation of the hip and outside the knee. This condition is best served by a level 1 stability shoe.

With Achilles tendonitis maximum shoe stability is necessary to turn the pronated foot into a more rigid lever arm. The increases the efficiency of both the Achilles tendon and the calf muscles. Additionally, heel lifts may be helpful. A level 1 stability shoe is recommended.

For shin splints, either medial (posterior tibial) or anterolateral, the long axis of the shoe should again exhibit maximum resistance to rotation. This will reduce the undesired forces on the lower leg. Level 1 stability shoes are indicated.

In the case of bunions or first metatarsal head pain, once again the shoe should have maximum resistance to pronation of the foot. This will reduce the translation of improper forces to the big toe as the shoe wearer moves through the push-off phase of the gait. The shoe should have a wide toe box to prevent pressure on the first metatarsal head. Level 1 stability is indicated.

In plantar fascitis, the pronation of the foot stretches the plantar fascia which causes soreness and tenderness on medial and plantar surfaces of the heel. Maximum stability: i.e. resistance to pronatiom is again helpful along with a good toe spring in the shoe to reduce stretching of the plantar fascia. Level 1 stability is recommended.

It should be emphasized that the instant invention is not in any way limited to the embodiments as they are described above but encompasses all embodiments as described in the scope of then following claims.

What is claimed as being new and desired to be protected by LETTERS PATENT of the United States is as follows:

1. A method for determining an appropriate shoe type for a user comprising the steps of:
    establishing a predetermined baseline temperature for a certain model of shoe;
    measuring a first axial torque of the shoe along the shoe's longitudinal axis;
    subjecting the shoe to a predetermined stressor;
    measuring a second axial torque of the shoe along the shoe's longitudinal axis;
    comparing said first axial torque and said second axial torque of the shoe; and
    calculating a fatigue factor for said predetermined stressor wherein said fatigue factor is the percentage difference between said first axial torque and said second axial torque.

2. The method according to claim 1, wherein said first axial torque and said second axial torque are measured in inch-pounds.

3. The method according to claim 1, wherein said predetermined stressor is an environmental temperature change.

4. The method according to claim 1, wherein said baseline temperature lies within the range of about between 50 and 70 degrees F.

5. The method according to claim 4, wherein said predetermined stressor is an environmental temperature change to the range that lies of about between 70 and 125 degrees F.

6. The method according to claim 5, wherein said first axial torque and said second axial torque are measured in inch-pounds.

7. The method according to claim 1, wherein said predetermined stressor is an addition of kinetic energy to the shoe.

8. The method according to claim 7, wherein said baseline temperature lies in the range of about between 50 and 70 degrees F.

9. The method according to claim 8, wherein said addition of kinetic energy to the shoe is provided by a user wearing the shoe for a predetermined amount of time.

10. The method according to claim 9, wherein additional kinetic energy is added to the shoe by the user performing a predetermined amount of exercise while wearing the shoe.

11. The method according to claim 10, wherein said first axial torque and said second axial torque are measured in inch-pounds.

12. The method according to claim 1, further including a classifying step after said calculating step; wherein the overall stability of the shoe places it within a group.

13. The method according to claim 12, wherein the groups are sorted by stability.

14. The method according to claim 12, further including an observing step after said classifying step, said observing step serving to analyze the subphases of the user's gait to determine which of said groups of shoe is appropriate for the user.

15. A method for determining an appropriate shoe type for a user comprising the steps of:

establishing a predetermined baseline temperature lying of about between 50 and 70 degrees F. for a certain model and brand of shoe;

measuring a first axial torque of the shoe along the shoe's longitudinal axis;

subjecting the shoe to a predetermined stressor, said predetermined stressor being an environmental temperature change to lie within the range of about between 70 and 125 degrees F.;

measuring a second axial torque of the shoe along the shoe's longitudinal axis;

comparing said first axial torque and said second axial torque of the shoe; and calculating a fatigue factor for said predetermined stressor wherein said fatigue factor is the percentage difference between said first axial torque and said second axial torque.

16. A method for determining an appropriate shoe type for a user comprising the steps of:

establishing a predetermined baseline temperature lying in the range of about between 50 and 70 degrees F. for a certain model of shoe;

measuring a first axial torque of the shoe along the shoe's longitudinal axis;

subjecting the shoe to a predetermined stressor, said predetermined stressor being an addition of kinetic energy to the shoe;

measuring a second axial torque of the shoe along the shoe's longitudinal axis;

comparing said first axial torque and said second axial torque of the shoe; and calculating a fatigue factor for said predetermined stressor wherein said fatigue factor is the percentage difference between said first axial torque and said second axial torque.

17. The method according to claim 16, wherein said addition of kinetic energy to the shoe is provided by a user wearing the shoe for a predetermined amount of time.

\* \* \* \* \*